US007851648B2

(12) United States Patent
Sohn et al.

(10) Patent No.: US 7,851,648 B2
(45) Date of Patent: Dec. 14, 2010

(54) METHOD FOR THE CONTINUOUS PRODUCTION OF ISOCYANATES

(75) Inventors: Martin Sohn, Mannheim (DE); Eckhard Stroefer, Mannheim (DE); Filip Nevejans, St. Gillis-Waas (BE); Ulrich Penzel, Tettau (DE); Hans-Juergen Pallasch, Ludwigshafen (DE); Rene Leuthold, Hohenbocka (DE); Andreas Brodhagen, Bierbeeg (BE); Andreas Woelfert, Bad Rappenau (DE); Wolfgang Mackenroth, Bad Duerkheim (DE); Markus Maurer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1548 days.

(21) Appl. No.: 10/539,802

(22) PCT Filed: Dec. 13, 2003

(86) PCT No.: PCT/EP03/14185

§ 371 (c)(1),
(2), (4) Date: Jun. 20, 2005

(87) PCT Pub. No.: WO2004/056756

PCT Pub. Date: Jul. 8, 2004

(65) Prior Publication Data

US 2006/0252960 A1 Nov. 9, 2006

(30) Foreign Application Priority Data

Dec. 19, 2002 (DE) ................ 102 60 082

(51) Int. Cl.
*C07C 249/00* (2006.01)
(52) U.S. Cl. .................................... 560/347
(58) Field of Classification Search ........... None
See application file for complete search history.

(56) References Cited

U.S. PATENT DOCUMENTS

| 2,683,160 | A |   | 7/1954  | Irwin |         |
|-----------|---|---|---------|-------|---------|
| 2,822,373 | A | * | 2/1958  | Beck  | 560/347 |
| 3,226,410 | A |   | 12/1965 | Hettich et al. | |
| 3,321,283 | A |   | 5/1967  | Ewald | |
| 3,381,025 | A |   | 4/1968  | Mitsumori et al. | |
| 3,544,611 | A |   | 12/1970 | Michelet et al. | |
| 3,574,695 | A |   | 4/1971  | Grant, Jr. et al. | |
| 3,801,518 | A |   | 4/1974  | Irwin et al. | |
| 3,912,600 | A |   | 10/1975 | Hatfield, Jr. et al. | |
| 6,576,788 | B1| * | 6/2003  | Penzel et al. | 560/347 |
| 7,084,297 | B2| * | 8/2006  | Woelfert et al. | 560/347 |

FOREIGN PATENT DOCUMENTS

| CA | 832 432 | 1/1970 |
|----|---------|--------|
| DE | 844 896 | 9/1952 |
| DE | 949 227 | 9/1956 |
| DE | 949 228 | 9/1956 |
| DE | 952 086 | 11/1956 |
| DE | 958 558 | 2/1957 |
| DE | 1 037 444 | 8/1958 |
| DE | 1 146 872 | 4/1963 |
| DE | 1 175 666 | 8/1964 |
| DE | 1 192 641 | 5/1965 |
| DE | 1 233 854 | 2/1967 |
| DE | 1 468 445 | 2/1969 |
| DE | 1 811 609 | 7/1969 |
| DE | 1 768 439 | 11/1971 |
| DE | 1 792 660 | 3/1972 |
| DE | 2 058 032 | 5/1972 |
| DE | 2 112 181 | 10/1972 |
| DE | 2 153 268 | 5/1973 |
| DE | 2 252 068 | 5/1973 |
| DE | 24 04 773 | 8/1975 |
| DE | 26 24 285 | 12/1977 |
| DE | 27 47 524 | 5/1978 |
| DE | 132 340 | 9/1978 |
| DE | 29 50 216 | 6/1980 |
| DE | 29 08 703 | 9/1980 |
| DE | 32 12 510 | 11/1982 |
| DE | 33 23 882 | 4/1984 |
| DE | 34 03 204 | 8/1985 |
| DE | 37 36 988 | 3/1989 |
| DE | 37 44 001 | 6/1989 |
| DE | 300 168 | 5/1992 |
| DE | 198 17 691 | 10/1999 |

(Continued)

OTHER PUBLICATIONS

Siefken, Von Werner. "Mono- und Polyisocyanate", Justus Liebigs Annalen der Chemie, vol. 562, pp. 6-136 1948.

(Continued)

*Primary Examiner*—Daniel M Sullivan
*Assistant Examiner*—Clinton Brooks
(74) *Attorney, Agent, or Firm*—Oblon, Spivak, McClelland, Maier & Neustadt, L.L.P.

(57) ABSTRACT

The invention relates to a process for preparing polyisocyanates by reacting organic amines with phosgene, wherein the reaction is carried out in at least three stages, with the first stage being carried out in a mixing apparatus, the second stage in at least one residence apparatus and the third stage in at least one separation apparatus and the pressure in each successive stage being lower than that in the previous stage.

18 Claims, No Drawings

FOREIGN PATENT DOCUMENTS

| | | | |
|---|---|---|---|
| DE | 10158160 | * | 11/2001 |
| DE | 100 27 779 | | 12/2001 |
| DE | 156 844 | | 12/2004 |
| EP | 0 065 727 | | 12/1982 |
| EP | 0 150 435 | | 8/1985 |
| EP | 0 289 840 | | 11/1988 |
| EP | 0 291 819 | | 11/1988 |
| EP | 0 570 799 | | 11/1993 |
| EP | 0 676 392 | | 10/1995 |
| EP | 0 716 079 | | 6/1996 |
| EP | 0 749 958 | | 12/1996 |
| EP | 0 830 894 | | 3/1998 |
| EP | 0 928 785 | | 7/1999 |
| EP | 1 078 918 | | 2/2001 |
| FR | 2 009 527 | | 2/1970 |
| GB | 763 535 | | 12/1956 |
| GB | 827 376 | | 2/1960 |
| GB | 1 034 285 | | 6/1966 |
| GB | 1 196 008 | | 6/1970 |
| GB | 1 212 249 | | 11/1970 |
| JP | 57-048954 | | 3/1982 |
| JP | 60-010774 | | 1/1985 |
| WO | 96/16028 | | 5/1996 |
| WO | 99/54289 | | 10/1999 |
| WO | WO99/54289 | * | 10/1999 |
| WO | WO03/045900 | * | 6/2003 |

OTHER PUBLICATIONS

Schauerte, K. et al. "Isocyanate", Polyurethane, Kunststoff Handbuch, vol. 7, pp. 76-88 1993.

Zehner, Peter et al. "Duesenreaktoren", Fortschr. Vert. Technik, vol. 23, pp. 373-393 1985.

Tosun, Gueray. "A Study of Micromixing in Tee Mixers", Ind. Eng. Chem. Res., vol. 26, pp. 1184-1193 1987.

Ullmanns Enzyklopaedie der technischen Chemie, vol. 13, pp. 351-353 1977.

Konstantinov, I. et al. "Kinetics of the Reactions of 2,4-Tolylene- and 4,4'-Diphenylmethanediamine Dihydrochloride Crystals with Phosgene Dissolved in Chlorobenzene", Zhurnal Prikladnoi Khimii, vol. 49, No. 3, pp. 596-599 1976.

* cited by examiner

METHOD FOR THE CONTINUOUS PRODUCTION OF ISOCYANATES

The present invention relates to a process for preparing aromatic or aliphatic isocyanates. Among aromatic isocyanates, preference is given to methylenedi(phenyl isocyanate) (MDI) and tolylene diisocyanate (TDI), while in the case of aliphatic isocyanates, preference is given to hexamethylene diisocyanats (HDI) and isophorone diisocyanate (IPDI) and others.

It is an object of the present invention to develop a two-stage or multistage process which gives isocyanates in very high chemical yields and with high space-time yields at a low phosgene holdup.

In the process of the present invention, the reaction between organic amine and phosgene is carried out in two or more stages in an inert solvent, preferably toluene, chlorobenzene, dichlorobenzene or a mixture of the latter two, and using an excess of phosgene, wherein the pressure is reduced between each of the stages and the first phosgenation stage comprises a static mixer, preferably a nozzle, the second stage comprises a residence apparatus and the third stage comprises a (reaction) column. The pressure upstream of the nozzle is preferably 3-70 bar, more preferably 15-45 bar. The residence reactor of the second stage is preferably operated at a pressure of 2.5-35 bar, preferably 15-35 bar. Downstream of the nozzle, the pressure is reduced to the pressure of the second stage by means of a regulating valve or some other device suitable for this purpose. It is also possible to use the natural pressure drop in the nozzle for reducing the pressure. The reactor of the first stage, usually a static mixer, can also be integrated into the reactor of the second stage, viz. a residence apparatus. The reactor of the third phosgenation stage, usually a column, preferably a reaction column, is preferably operated at a pressure of 2-20 bar, preferably 3.5-16 bar. Downstream of the reactor of the second stage, the pressure is reduced to the pressure of the reactor of the third stage by means of a regulating valve or some other device suitable for this purpose. Once again, a natural pressure drop may be sufficient to achieve the reduction in pressure. As reactor of the third stage, preference is given to using a (reaction) column as is described, for example, in WO 99/54289 (DE 19817691).

The preparation of isocyanates from amines and phosgene is known. The reaction is, depending on the type of amine, carried out either in the gas phase or in the liquid phase, either batchwise or continuous preparation of organic isocyanates by reaction of primary organic amines with phosgene has been described many times and is carried out on a large industrial scale (cf., for example, Ullmanns Enzyklopädie der Technischen Chemie, Volume 7 (Polyurethane), $3^{rd}$ revised edition, Carl Hanser Verlag, Munich-Vienna, p. 76ff (1993).). The aromatic isocyanates TDI (tolylene diisocyanate) and MDI methylenedi(phenyl isocyanate) and PMDI (polymethylene-polyphenylene polyisocyanate) and mixtures of the latter two and the aliphatic isocyanates HDI (hexamethylene diisocyanate) and isophorone diisocyanate (IPDI) in particular are prepared industrially around the world.

Present-day industrial syntheses of the aromatic diisocyanates MDI and TDI and the aliphatic diisocyanates HDI and IPDI are carried out virtually exclusively in continuous processes. A continuous process for carrying out the reaction in a plurality of vessels through which the reaction mixture flows continuously is described, for example, in DE 844896. In general, the continuous embodiment of the process is carried out in two stages. In the first stage of the phosgenation, the amine is reacted with phosgene to form the corresponding carbamoyl chloride and hydrogen chloride and the amine hydrochloride. The reaction between amine and phosgene is very fast, strongly exothermic and proceeds even at very low temperatures. To minimize by-product and solids formation, amine and phosgene, each in an organic solvent if desired, therefore have to be mixed quickly, which is why the first phosgenation stage is generally carried out in a mixing apparatus, preferably a nozzle. The second stage of phosgenation comprises both the decomposition of the carbamoyl chloride to form the desired isocyanate and hydrogen chloride and the phosgenation of the amine hydrochloride to form the carbamoyl chloride. The temperature of the second phosgenation stage is generally higher than that of the first.

The reaction of amine and phosgene in the liquid phase is very fast at all industrially customary temperatures and pressures. For this reason, good mixing of the reactants is sought, in order to suppress secondary reactions. The phosgenation of primary amines in a mixing reactor as first stage of the phosgenation has been described many times.

Mixing apparatuses can basically be classified as dynamic mixers, e.g. stirrers and turbines, and static mixers, rotor-stator systems such as Kenics mixers, Schaschlik mixers, SMV mixers, and jet mixers such as nozzles or T-mixers (Chem. Ing. Tech. MS 1708/88, Fortschr. Verf. Technik 23, 1985, 373, Ind. Eng. Chem. Res. 26, 1987, 1184).

Known mixing apparatuses include, in particular, nozzles such as annular slit nozzles (DE 1792660), annular hole nozzles (DE 3744001), smooth-jet mixing nozzles (EP 0065727), fan jet nozzles (DE 2950216), angled jet chamber nozzles (DD 300.168), three-stream nozzles (DD 132340), countercurrent mixing chambers (DE-C 1146872), fluid backup nozzles (FR 69428), Venturi mixing nozzles (DE-B 1175666). In-line mixers (U.S. Pat. No. 3,321,283), centrifugal mixing pumps or reaction mixing pumps (EP 0291819), tubular reactors (U.S. Pat. No. 3,226,410) or microstructure mixers (EP 0928785) are also known. CA 832432 describes the use of ultrasound waves for mixing.

EP 0830894 describes a mixing reactor for the phosgenation of primary amines, in which the inlet for one substance is located in the axis of the mixing chamber and the inlet for the other substance (or substances) is configured as a multiplicity of nozzles arranged rotationally symmetrically around the axis of the mixing chamber, with each of these nozzles having a pin which is movable in the direction of the nozzle axis and can free the nozzle of adhering solids.

DD 132340 describes a process for the phosgenation of amines to form monoisocyanates, diisocyanates and polyisocyanates under superatmospheric pressure and at elevated temperature in the presence of a uniform solvent, in which an amine/monochlorobenzene mixture and a phosgene/monochlorobenzene mixture are fed in parallel as a plurality of substreams into a reactor, with part of the phosgene/monochlorobenzene mixture being introduced centrally and the amine/monochlorobenzene mixture being introduced around this central stream and the amine/monochlorobenzene mixture being in turn enclosed by a phosgene/monochlorobenzene mixture. The polyamine/monochlorobenzene mixture is, for example, fed as an annular stream into the phosgenation reactor at 150° C. Before entry into the reactor, a rotating motion is imparted to the mixture by means of an appropriate twist-inducing device. In and around the polyamine/monochlorobenzene mixture, a phosgene/monochlorobenzene mixture which has been heated to 150° C. is fed as reactant into the reactor. The relative velocity of the two reactants is about 15 m/s.

For the second phosgenation stage, which may simultaneously be used as phase separation vessel, a multiplicity of apparatuses has also become established. The preparation of isocyanates from the corresponding amines by phosgenation is carried out in stirred vessels (e.g. DE-A 1468445), in cascades of stirred vessels (DE-C 844896), in packed reaction columns (e.g. WO 99/54289) or in unpacked columns (e.g. Ullmanns Encyclopädie der technischen Chemie, 4$^{th}$ edition (1977), pages 351 ff). In addition, a circulating mode of operation is also realised by use of loop reactors in order to provide a sufficient residence time for complete conversion at a limited reaction volume (and holdup).

The first stage of the isocyanate synthesis is frequently carried out at a very low temperature and the second stage at significantly higher temperature in a residence apparatus. This mode of operation is frequently described as cold-hot phosgenation and is described, for example, in W. Siefken, Liebigs Analen der Chemie 562 (1949), page 96. Firstly, a suspension of the intermediates carbamoyl chloride and amine hydrochloride is prepared at low temperature, in particular at 0° C. or room temperature, but at most 60° C., and this is then converted into the isocyanate at higher temperatures, in particular in the range 100-200° C., in a residence apparatus. Such two-stage processes are described in the Kunststoffhandbuch, Volume 7 (Polyurethane), 3$^{rd}$ revised edition, Carl Hanser Verlag, Munich-Vienna, p. 76ff (1993), and, for example, in DE 2058032, DE 2153268, DE 2908703, DE 1233854.

DE 949227 describes a cold-hot phosgenation process for the continuous preparation of isocyanates by reaction of amines with phosgene in the liquid phase in the presence of a solvent, in which a solution or slurry of the amine in an inert solvent is continuously combined with liquid phosgene or a solution of phosgene in an inert solvent in a mixing apparatus with intensive stirring and without external cooling in the cold phosgenation and the reaction mixture obtained in this way is then subjected to the hot phosgenation. As mixing apparatuses, turbomixers and centrifugal pumps and mixing apparatuses having moving mechanical parts in general are claimed. The residence time in the mixing apparatus ranges from a few seconds to one minute.

DE 949228 describes a cold-hot phosgenation process for the continuous preparation of monocyclic aromatic diisocyanates (e.g. tolylene diisocyanate), in which a suspension is prepared continuously from the parent amine of the isocyanate and the total amount of the solvent used in the phosgenation, the suspension is continuously reacted cold with phosgene, the reaction product is subsequently pushed continuously through one or more vertical or slanted tubes known as phosgenation towers in which the material is, if desired with introduction of gaseous phosgene, heated to the phosgenation temperature and the solution is subsequently freed of dissolved phosgene by stripping with a dry inert gas stream in a column. o-Dichlorobenzene was used as solvent. The cold phosgenation is carried out at 0° C. in a stirred vessel, the reaction mixture is then preheated to 30° C. and finally reacted at 170° C. in the hot phosgenation in two phosgenation towers connected in series to give the isocyanate. Gaseous phosgene is introduced at the bottom of the second phosgenation tower. The hydrogen chloride/phosgene/solvent mixture taken off at the top of the two phosgenation towers is partially condensed in the respective condenser at the top of the respective phosgenation tower and is recirculated to the bottom. The incondensible gas comprising phosgene and hydrogen chloride is passed to a phosgene/hydrogen chloride separation unit or to disposal. The liquid and completely phosgenated reaction product leaving the second phosgenation tower runs into a bubble cap tray column and is there freed of dissolved phosgene by stripping in countercurrent with a stream of nitrogen. The vapor taken off at the top is passed to a condenser and condensed solvent is recirculated to the top of the column. At the bottom of the column, the reaction product in the solvent is taken off and passed to distillation.

DE 952086, too, describes a cold-hot phosgenation. The hot phosgenation is carried out in upright reaction towers filled with Raschig rings or other packing elements. The cold phosgenation is carried out at 0° C. and the hot phosgenation is carried out using a rising temperature profile from 120° C. to 160° C.

In DE 958558, the circulated solvent is introduced not at the lower end of the reaction towers but in the cold phosgenation stage. Dilution of the reaction product from the cold phosgenation gives the advantage of a solution having a relatively low viscosity instead of a viscous suspension of carbamoyl chloride and amine hydrochloride.

DE 2058032 also describes a cold-hot phosgenation. The hot phosgenation is carried out in horizontal tube reactors at up to about 200° C., and the reaction mixture from the cold phosgenation is fully reacted in the hot phosgenation stage with continual mechanical mixing and a slowly rising temperature profile. The cold phosgenation is carried out at 0° C.

U.S. Pat. No. 2,908,703 describes a two-stage process for preparing aromatic isocyanates, in which the first reaction step is carried out at 60-90° C., preferably 70-85° C., using chlorobenzene as solvent, and the second reaction step is carried out at a temperature which is high enough to decompose the intermediate to form the isocyanate. A solution of amine in an organic solvent, preferably chlorobenzene or o-dichlorobenzene, and gaseous phosgene are introduced simultaneously into a stirred and heated reactor so that a saturated phosgene solution is formed and the phosgene excess is at least 50% over the stoichiometric amount of phosgene for the amine/phosgene reaction. The reaction mixture is subsequently heated to the decomposition temperature of the carbamoyl chloride and amine hydrochloride. The isocyanate formed is finally separated off by fractional distillation or other methods. As an alternative to this batch procedure, the process described can also be carried out continuously by carrying out the first reaction step in a first reactor and the second step in a second reactor. The reaction is generally carried out at atmospheric pressure. The concentration of the amine in the organic solvent is 2-20% by weight, preferably 5-10% by weight. Higher concentrations lead to formation of by-products, in particular ureas and polyureas.

In U.S. Pat. No. 3,381,025, the phosgenation of an organic primary amine to form the corresponding isocyanate is carried out in two stages at <60° C. in the first stage and 100-190° C. in the second stage. A mixture of the inert solvent, excess phosgene and the hydrogen chloride formed is taken off from the second reaction stage and the hydrogen chloride is separated off from this mixture by cooling the mixture to −20° C. The cold liquid mixture of phosgene and solvent obtained is recirculated to the first reaction stage.

DE 2153268 describes a process for a continuous cold phosgenation of organic primary amines by reaction with a solution of phosgene in an inert solvent in a multistage, not self-priming centrifugal pump. The centrifugal pump at the same time conveys the resulting reaction mixture to the subsequent hot phosgenation stage. The phosgene solution enters the pump at from −105° C. to +25° C. and the amine solution enters it at from 50 to 100° C. The reaction mixture leaves the pump at from 50 to 110° C. The concentration of the amine solution is from 5 to 40% by weight, and that of the phosgene solution is 20-65% by weight. The amount of phosgene is at least 1 mol, preferably 1.5-3 mol, per mol of amine group.

A disadvantage of the two-stage procedure with a low temperature in the first stage and a high temperature in the second stage (cold-hot phosgenation) is the low reaction rates and thus low space-time yields owing to the low temperatures in the first phosgenation stage. The low temperatures (high solubility of phosgene) and the long reaction times (large reactors) additionally imply a high phosgene holdup, which is undesirable from a safety point of view. Low temperatures are also problematical because of the massive precipitation of the carbamoyl which is formed as an intermediate and decomposes rapidly at elevated temperatures. This brings with it the risk of blockages and the formation of caked material. Furthermore, cooling of the reactants and later heating of the reaction mixture is energetically disadvantageous. To achieve economical space-time yields, operation at elevated temperature in all stages is necessary in industrial processes for preparing organic isocyanates by phosgenation of primary organic amines. However, the solubility of the phosgene in the reaction mixture and therefore the phosgene excess available for the reaction decreases at high temperatures, since the reaction generally takes place in the liquid phase. A high excess of phosgene is nevertheless necessary to achieve high yields of isocyanate. EP 0716079 describes the influence of pressure and temperature on the reaction and the phosgene excess. The lowering of the phosgene excess at elevated temperatures is generally countered by means of an increased reaction pressure. DE-A 1768439 describes a process for the continuous preparation of organic isocyanates which employs a combination of high temperature above 180° C. and a high pressure of from 20 to 150 atm together with a high phosgene concentration in the reaction zone. The amount of amine introduced is from 2.5 to 5.5 times the stoichiometric amount. As a result of the extremely high pressure and the very high temperature, acceptable space-time yields can be achieved. The residence time of the reactants in the reaction zone is 5-60 s. The preferred solvent is chlorobenzene. A disadvantage of the process is the reduced yield and quality caused by the increased formation of by-products, in particular ureas, as a result of the high temperature. In addition, industrial pressure apparatuses are very expensive and are problematical because of the high toxicity of phosgene. Carrying out the reaction of amine with phosgene at high pressure also has the disadvantage that, in accordance with Henry's law, not only the phosgene concentration but also the hydrogen chloride concentration in the liquid phase is increased. The increased formation of amine hydrochlorides is, however, undesirable since their phosgenation is, according to generally accepted opinion, very slow and therefore represents the rate-determining step of the overall reaction. This leads to very long residence times and large phosgene holdups.

EP 0065727 describes a process using a nozzle and tube reactor. A process for the continuous preparation of organic monoisocyanates and polyisocyanates in a single-stage reaction by continuous combination of solutions of primary monoamines or polyamines in inert organic solvents with excess amounts of phosgene dissolved in an inert organic solvent at pressures of from 10 to 1000 bar, preferably from 25 to 150 bar, and temperatures of from 120 to 300° C., preferably from 150 to 250° C., in a mixing zone and, if desired, a downstream reaction zone and continuous work-up, with the phosgene solution, which is used in excess, being continuously placed in a mixing zone and the amine component, which is used in a deficiency, being injected by means of a smooth-jet nozzle, is described. The smooth-jet nozzle which is essential to the process has an internal diameter of 0.1-30 mm. A differential pressure of at least 0.5 bar, preferably 1-200 bar, in particular 3-50 bar, is maintained in the phosgene solution injected. The molar ratios of phosgene to amino groups are from 2:1 to 30:1, preferably from 3:1 to 18:1. The after-reaction zone can be a tube reactor, a shell-and-tube reactor or, for example, a cascade of stirred vessels. The mean residence time in the mixing vessel and in the downstream reaction zone is from 5 seconds to 5 minutes. The reaction mixture leaving the after-reaction zone is depressurized to atmospheric pressure in one or more stages in a depressurization vessel, resulting in a temperature drop of 50-150° C. Gas and liquid phases are separated in the depressurization vessel. As solvents, preference is given to using chlorobenzene or o-dichlorobenzene.

GB 827376 describes a continuous process for preparing aromatic isocyanates by reacting an amine in free form in a solvent or as a salt which readily decomposes to the amine and is suspended in the solvent with a solution of phosgene in an inert solvent at a pressure of greater than $3*10^5$ Pa, with the reactants being introduced simultaneously with mixing into the lower end of a vertical tube reactor in which the reaction products rise rapidly to the upper end. The liquid phase is collected in a container from which it is taken off to isolate the isocyanate. This container can be a phase separation apparatus which is operated under the same pressure, is connected via an overflow tube to the liquid outlet and has a throttle valve in the liquid outlet. The liquid collected in the container is fed into a column which is operated under atmospheric or superatmospheric pressure and at elevated temperature, so that residual phosgene and hydrogen chloride are separated off at the top in gaseous form. The excess phosgene is condensed out (preferably by means of cooling water) from the hydrogen chloride/phosgene mixture separated off in the container, and the hydrogen chloride which has been separated off in this way is depressurized and discharged. The reactants are fed by means of one joint pump or two separate pumps into the tube reactor or else mixed in a Venturi mixing nozzle, preferably one having separate inlets for the two reactants, and from there introduced into the tube reactor. The temperature in the tube reactor is given as 80-200° C., the pressure is greater than $3*10^5$ Pa, at most the vapor pressure of the reaction mixture and preferably $15-20*10^5$ Pa.

U.S. Pat. No. 3,226,410 describes a continuous process for preparing aromatic isocyanates by mixing a stream of an aromatic amine into a phosgene stream in a tube reactor at Reynolds numbers of greater than 2100 (preferably 5000-2000000) and temperatures of 60-90° C., preferably 80-85° C. The amount of phosgene is at least 1 mol, preferably from 6 to 12 mol, per mol of amine. The reaction solution is then, if desired after preheating, fed into a second reactor, in particular a vessel or a column, which is at from 110 to 135° C., preferably from 110 to 120° C. The amine concentration is from 2 to 25% by weight, preferably from 5 to 10% by weight, and the phosgene concentration is from 10 to 100% by weight, preferably from 10 to 60% by weight. The pressure at which the phosgene stream is introduced into the tube reactor is 50-170 psig; the pressure of the amine stream has to be greater in order to prevent backmixing. The liquid phase comprising isocyanate, solvent, relatively small amounts of by-products, hydrogen chloride and phosgene dissolved in a solvent is taken off from the second reactor separately from the gas phase comprising hydrogen chloride, solvent, phosgene and traces of the isocyanate. Solvents used are chlorinated hydrocarbons which are inert and have a boiling point lower than that of the isocyanate. Particular preference is given to chlorobenzene.

The second reactor, which has a pressure of 45 psig or higher, is followed by a residence vessel and a buffer vessel from which the liquid phase is conveyed under level control to a column for removing excess phosgene. Phosgene, hydrogen chloride and solvent are taken off at the top and recirculated to the phosgene container. The bottom product comprising isocyanate and solvent is conveyed to a distillation, preferably a single-stage distillation, to separate off the solvent. The solvent which has been separated from the isocyanate is used for absorption of the remaining phosgene from the hydrogen chloride stream. The phosgene taken off in the second reactor and in the buffer vessel is condensed in two stages and recirculated to the phosgene container. The uncondensed phosgene/hydrogen chloride mixture is conveyed to a phosgene absorber into which solvent recovered in the solvent separation is fed. The gas which has not been absorbed, mainly hydrogen chloride, is subsequently reacted with water in an absorber to form aqueous hydrochloric acid.

The tube reactor should be constructed as a plug flow reactor without deflection plates, pockets or other internals which can produce dead zones so that settling of solids is prevented. The high Reynolds numbers and the design of the reactor as straight tubes are intended to lead to the liquid continually keeping the walls free of caked material.

DE 952086 describes a process for preparing isocyanates from primary amines or their salts and phosgene, in which the reactants are, in the hot phosgenation in the presence of a solvent or diluent, passed continuously from the bottom upward through a vertical or slanted, heated tube. After the reactants have passed through this first reaction tube, they can, if appropriate, pass through a second, likewise vertical reaction tower with addition of further phosgene to complete the reaction. The advantage of vertical reaction towers which are filled with Raschig rings or other packing elements to prevent rapid degassing is that the rate of isocyanate formation is increased as a result of the increased phosgene concentration at the entry point for the reactants located at the bottom due to the hydrostatic pressure of the column of liquid. o-Dichlorobenzene is named as solvent. The process is a two-stage process with a cold phosgenation as first stage and a hot phosgenation as second stage. The cold phosgenation is carried out at 0° C. and the hot phosgenation is carried out with a rising temperature profile from 120° C. to 160° C.

Disadvantages of this process are the fundamental weak points of cold-hot phosgenation and also the low achievable pressure. Considerably higher pressures and thus phosgene concentrations in the liquid phase can be obtained by means of pressure vessels and regulating valves. A further disadvantage is the packing elements used in the tube reactors, since the solid intermediates carbamoyl chloride and amine hydrochloride formed and precipitated in the cold phosgenation can easily lead to blockages and thus to low availability of the plant.

DE 2058032 describes a process for preparing isocyanates from amines and phosgene in the presence of an inert solvent, in which the reaction mixture is treated at 0° C. in the cold phosgenation and is subsequently reacted fully at up to about 200° C. in the hot phosgenation, with the reaction mixture from the cold phosgenation being conveyed in the hot phosgenation stage through a horizontal reaction zone with continual mechanical mixing and a slowly rising temperature profile. As heatable reaction vessel for the hot phosgenation, a horizontal tube through which a shaft provided with tube devices extends in the longitudinal direction and which has separately heatable sections of wall heating is claimed. A natural convection vaporizer (thermosyphon) can be located at the end of the tube reactor. An arrangement of three reaction tubes connected to one another in the shape of a U (system of communicating tubes) is also described. The cold phosgenation is carried out in the first, vertical tube, the hot phosgenation is carried out in the horizontal tube and the degassing, i.e. the removal of hydrogen chloride phosgene from the reaction mixture, is carried out in the second vertical tube. Transport pumps and regulating valves can be omitted in such a system, since the product flow is established according to the inflow rate.

DE 2747524 describes a continuous process for preparing aromatic isocyanates in which heat is introduced into the reactor at a rate so that added phosgene does not lead to cooling and thus to caking of the carbamoyl chlorid intermediate on the reactor wall. A plug flow reactor comprising two coaxial tubes into which the two reactants amine and phosgene in an inert organic solvent are introduced in countercurrent, each isolated from the other, and are mixed at the end of the internal tube is described. Backmixing into the feed zone is said to be prevented so as to minimize by-product formation. Heating is by means of a steam jacket in order to prevent blocking of the mixing zone by the carbamoyl chloride intermediate. Temperatures of 90-140° C. are said to be necessary; in general, temperatures of 90-200° C. are indicated. The initial temperature is, however, 60-90° C. Practical considerations determine the upper limit to the temperature. 2 atmospheres gauge is indicated as a convenient pressure. The amine concentration in the inert solvent is given as from 2 to 20%, preferably from 5 to 10%. Dichlorobenzene is preferred as inert solvent.

A tube reactor is also the preferred apparatus in the process described in WO 96/16028 for the preparation of isocyanates using isocyanate as solvent. WO 96/16028 describes a continuous, single-stage process in which the primary amine, optionally dissolved in an inert, organic solvent, is reacted with phosgene dissolved in the isocyanate in a concentration of 10-60% by weight, based on the isocyanate/phosgene solution, at 60-180° C. and pressures of 1-30 bar to form the corresponding isocyanate, with the molar ratio of phosgene to amine used being from 4:1 to 1:1 and the isocyanate used as solvent being free of solids and having a hydrolyzable chlorine content of less than 2%.

DE 19817691 describes a two-stage process for preparing mixtures of diphenylmethane diisocyanates (MDI) and polyphenylene-polymethylene polyisocyanates (PMDI) having a reduced content of chlorinated by-products and a reduced iodine color number by two-stage reaction of the corresponding mixtures of diphenylmethanediamines (MDA) and polyphenylene-polymethylene-diamines (PMDA) with phosgene in the presence of at least one organic solvent at elevated temperature, removal of the excess phosgene and solvent after the phosgenation is complete and thermal treatment of the reaction product with the molar ratio of phosgene to hydrogen chloride in the residence apparatus of the second stage of the phosgenation being 10-30:1 in the liquid phase and at the same time 1-10:1 in the gas phase. The carbamoyl chlorides and amine hydrochlorides formed in the first stage of the phosgenation, viz. static mixer, pass through a residence apparatus in the second stage of the phosgenation in which the amine hydrochlorides are phosgenated to the corresponding carbamoyl chorides and the carbamoyl chlorides are dissociated into the corresponding isocyanates and hydrogen chloride. The temperature of the first stage is usually from 40 to 150° C., preferably from 60 to 130° C., particularly preferably from 90 to 120° C. Static mixers employed for the first stage are, in particular, nozzles. As residence apparatus for the second stage, use is made of stirred apparatuses, cascades of stirred vessels and particularly preferably a column, in particular a reaction column usually having <10 theoretical plates. It is particularly advantageous to operate this column in countercurrent. The temperature at the bottom of the column is preferably from 80 to 120° C., particularly preferably from 90 to 110° C. The pressure at the top of the column is preferably from 1.0 to 4.7 atm (gauge), particularly preferably from 2.0 to 3.7 atm (gauge).

A disadvantage of this process is that the amine hydrochloride phosgenation and the carbamoyl chloride decomposition are carried out in one and the same reactor, which leads to prolonged residence times and higher phosgene holdups.

U.S. Pat. No. 3,544,611 describes a process for preparing organic isocyanates at a high pressure of from 10 to 50 bar. It was surprisingly found that carrying out the reaction at relatively high pressures of at least 10 atm gauge leads to higher yields of isocyanate. Furthermore, higher pressures aid the hydrogen chloride/phosgene separation. The first reaction step of the isocyanate preparation, viz. the reaction between amine and phosgene to form the carbamoyl chloride intermediate, is carried out in a loop reactor (mixing circuit). The second reaction step, viz. the decomposition of the carbamoyl chloride to form the isocyanate, occurs in a reaction column located downstream of the mixing circuit. A hydrogen chloride-phosgene mixture is obtained at the top of this column. Phosgene is condensed in two stages from this mixture. The phosgene which has been condensed out is recirculated to the top of the column. At a liquid offtake in the enrichment section of the column, phosgene is taken off and recirculated to the reaction (the mixing circuit).

The remaining phosgene is separated off from the reaction mixture taken off at the bottom of the reaction column in a further column. In the latter, phosgene is taken off at the top, condensed in two stages in a manner analogous to the first column and recirculated to the reaction in the mixing circuit. The reaction to give the isocyanate is finished in the reaction column.

DE 3736988 describes a continuous process for preparing organic monoisocyanates or polyisocyanates in a single-stage reaction by reacting the amine dissolved in an organic solvent with phosgene dissolved in an organic solvent in a reaction column at below 150° C. The reaction mixture is allowed to pass continuously through the reaction column from the bottom upward. The reaction column has at least 10 chambers separated from one another by perforated plates. The concentration of the amine in the inert solvent is 5-40% by weight, preferably 7-20% by weight. Preferred solvents are chlorobenzene or dichlorobenzene or mixtures thereof. Phosgene is used as a 30-65% strength by weight, preferably 40-65% strength by weight, solution in the inert solvent. The equivalence ratio of amine to phosgene is from 1:1.5 to 1:7, preferably from 1:2 to 1:5. The temperature at the top of the column is preferably 70-130° C., particularly preferably 90-125° C., and not more than 150° C. The mean residence time in the reaction column is not more than 120 minutes, preferably not more than 60 minutes. The pressure in the column is 1.2-3 bar abs, preferably 1.5-2.5 bar abs.

DE 3744001 likewise proposes a perforated plate column having >10 perforated plates, preferably 20-50 perforated plates, as residence apparatus through which the reaction mixture flows from the bottom upward at a liquid velocity of 0.05-0.4 m/s, preferably 0.1-0.4 m/s, and a gas velocity of 2-20 m/s, preferably 3.5-10 m/s, and a residence time of not more than 120 minutes, preferably not more than 60 minutes. The horizontally installed perforated plates form 10-50 chambers. The temperature at the top of the reaction column is less than 150° C., preferably 70-130° C., particularly preferably 90-125° C. The pressure at the top of the column is 1.2-3 bar (abs.), preferably 1.5-2.5 bar (abs.). A mixing nozzle is claimed for the first phosgenation stage.

EP 0291819 describes a two-stage process for preparing isocyanates by cold-hot phosgenation, in which a mixer having a rotary disk is used for the cold phosgenation and phosgenation towers are preferably used for the hot phosgenation. The phosgenation towers are operated at atmospheric pressure or a slightly superatmospheric pressure of up to 1.5 atm gauge. It is particularly advantageous to allow the reaction mixture from the cold phosgenation leaving the mixing apparatus to enter a heatable tower continuously at the top or the bottom and complete the reaction by introduction of heat. To set a particular temperature profile, a plurality of towers can be connected in series or a combination of towers and vessels can be used.

In DE 2112181 (U.S. Pat. No. 3,829,458), organic isocyanates are prepared continuously from primary organic amines and Phosgene in an inert organic solvent in one or more reaction vessels which contain packing and through which the reactants flow in cocurrent in a transition stream. The transition stream consists of an amine-containing, liquid organic phase and a phosgene-containing gas phase. The reaction takes place at reaction temperatures in the range from 50 to 220° C. In the case of incomplete reaction, the reaction mixture is circulated a number of times through the packed column. A disadvantage of this process is the high susceptibility of the packed column to blockages caused by solids such as carbamoyl chloride, amine hydrochloride, ureas, etc., being deposited on the packing elements. Furthermore, packed columns have a high pressure drop, which results in high temperatures at the bottom and thus high thermal stress on the reaction mixture and the isocyanate formed, leading to increased by-product formation and a reduced yield.

In many processes, the reaction of phosgene and amine is carried out in a loop reactor or circulating reactor in which not only the feed streams of amine and phosgene, if desired in a solvent, but also at least part of the reaction mixture are recycled. This dilution by recirculation of the reaction mixture formed serves mainly to control the temperature and to achieve better removal of heat so as to set low temperatures. The reaction between amines and phosgene is strongly exothermic. In the cases of unfavorable reaction conditions and configuration of the apparatus, higher temperatures cause increased by-product formation which, for example in the case of tolylene diisocyanate (TD), lead to a decrease in yield and formation of tar. Main by-products formed are ureas.

DE 2624285 (BASF) describes a mixing circuit process for the continuous preparation of organic isocyanates from organic amines and phosgene in the presence of organic solvents, in which the phosgene is mixed into the circulated reaction solution and the reaction mixture obtained and the amines or amine solution are fed into the mixing and reaction zone in such a way that an energy dissipation density of from 5 to 1000 kJ per m$^3$ of recirculated reaction mixture plus introduced amine solution is produced. The reaction is carried out at from 90 to 220° C., preferably from 120 to 180° C., and in a pressure range from 1 to 10 bar, preferably from 1 to 3 bar. The residence times are from 10 to 180 minutes. The molar ratio of amine to phosgene is such that from 1 to 10 mol, preferably from 1.3 to 4 mol, of phosgene per amino group are present in the reaction mixture. The yields are from 88 to 98% by weight, based on the amine used.

The mixing circuit process described in DE 2624285 is developed further in EP 0150435. In the process for the continuous preparation of organic isocyanates by reaction of organic amines with phosgene in the presence of organic solvents, with hydrogen chloride being separated off and the reaction mixture being partly circulated, the hydrogen chloride content of the reaction mixture recirculated to the addition of amine after the hydrogen chloride has been separated off is, prior to the addition of amine, equal to or less than 0.5% by weight, preferably from 0.01 to 0.4% by weight, based on the total weight of the reaction mixture, and the molar ratio of phosgene to amino groups of the organic amines is 12-200:1. The reaction is carried out at 100-220° C., preferably 120-180° C., and in a pressure range of 5-100 bar, preferably 15-50 bar.

DE 3403204 describes a process for the continuous preparation of organic isocyanates, preferably polyisocyanates, by reaction of organic amines, preferably polyamines, with phosgene in the presence of organic solvents under superatmospheric pressure, e.g. from 5 to 100 bar, and elevated temperatures, e.g. from 100 to 220° C., with the reaction mixture being partly circulated, preferably by the natural convection principle, and the hydrogen chloride content of the reaction mixture prior to the addition of amine being less than 0.5% by weight, based on the total weight of the reaction mixture, and the molar ratio of phosgene to amino groups of the organic amines being 12-200:1.

DE 3212510 describes a process for the continuous preparation of organic isocyanates. The primary organic amine is brought into contact in a virtually dispersed state with an excess of phosgene at a gauge pressure of 10 kg/cm$^2$, approximately 10 bar, and a temperature of from 60 to 100° C., resulting in formation of a corresponding organic carbamoyl chloride from the organic amine and hydrochloride formed as intermediate. Hydrogen chloride is formed as by-product. In this first stage of the reaction, from 30 to 70% of the carbamoyl chloride is converted into isocyanate. The reaction mixture is maintained at a gauge pressure of 10 kg/cm$^2$ and a temperature of from 120 to 160° C., so that the hydrochloride is converted into carbamoyl chloride and the conversion of the carbamoyl chloride into isocyanate is complete. The reaction takes place in a circulation reactor (circulation line) or in a tank-shaped reaction vessel. In the first case, the phosgene is allowed to circulate together with the solvent in a tubular circulation line and the amine is mixed in in this (mixing circuit). The residence time in the first stage is 30-120 minutes and that in the second stage is 10-120 minutes. ortho-Dichlorobenzene is chosen as solvent.

GB 763535 and DE 1811609 likewise describe loop reactors or circulation reactors (mixing circuits as reaction system). The organic isocyanate is prepared by reacting an amine with phosgene in a single-stage continuous reaction with circulation of isocyanate, solvent and unreacted phosgene. The pressure described as sufficient in the process described in GB 763535 is 5-20 pounds per square inch, the reaction temperature is 90-180° C., the TDA concentration in the solvent is 5-30%, the stoichiometric excess of phosgene is at least 25%, preferably 70-110%, and the solvents used are chlorinated aromatic hydrocarbons, preferably o-dichlorobenzene. In DE 1811609, the organic amine, if desired in ortho-dichlorobenzene or another solvent, and an excess of phosgene are mixed under high shear stress into the circulating reaction mixture, by which means conditions which advantageously deviate from GB 763535 can be set owing to the mixing. The reaction pressure is preferably at least 1.8-14*10$^5$ Pa, preferably 4.2*10$^5$ Pa or 3.5*10$^5$ Pa. The reaction temperature is stated to be preferably 102-130° C. and, in the case of toluenediamine, preferably 90-120° C. The excess of phosgene is 50-200%, preferably 70%.

DE 1037444 (U.S. Pat. No. 2,822,373) describes a continuous process for preparing organic isocyanates, in which a solution of the organic amine in an inert solvent is reacted with a solution of phosgene in an inert solvent at from 90 to 180° C. in a reaction zone in which superatmospheric pressure and turbulent flow prevail. The reaction solution is then depressurized into a zone at a lower pressure, usually atmospheric pressure, and hydrogen chloride and phosgene are taken off as a gaseous mixture. The isocyanate is separated from the solvent by distillation. In the process described, the amine solution is introduced into a pumped circulation line, the circulating mixture is heated downstream of the reaction zone by means of a heat exchanger and is then depressurized via a throttle valve into a tank-shaped residence vessel. From this, the reaction mixture is either taken out for the pumped circuit or partly discharged for removal of solvent and recovery of the isocyanate. The solvent is condensed from the gaseous mixture of hydrogen chloride, excess phosgene and solvent taken off from the reservoir in a condenser and is returned to the reservoir. Preferred pressures in the pumped circulation line are given as 5-20 pounds per square inch. The amine concentration in the solvent is 5-30% by weight, and the amount of phosgene is at least 1.25 mol per amino group of the amine. The preferred solvent is stated to be ortho-dichlorobenzene.

U.S. Pat. No. 3,574,695 describes an improved continuous process for preparing organic isocyanates. The residence times can be shortened by treating the product from the first reaction zone in the second reaction zone with at least 0.75 mol of phosgene per equivalent of organic amine added in the first reaction zone. The residence time in this second reaction zone is 5-45 minutes at a temperature of at least 130° C. A gaseous mixture of hydrogen chloride and phosgene and a liquid solution of the organic isocyanate in the solvent are continuously taken off from the second reaction zone.

GB 1034285 describes a continuous process for preparing organic isocyanates by reaction of phosgene with a primary polyamine in the presence of an inert organic solvent, with the reactants being fed separately into a tube reactor and brought into contact there and a mixture of the same solvent, the reaction mixture and phosgene being recirculated through this tube reactor. As reactor, it is possible to use an assembly of two cylindrical vessels between which the reaction mixture is circulated or an annular tube reactor. The reaction mixture can be stirred by means of stirrers. The temperature in the tube reactor is 8-50° C. The pressure is atmospheric pressure or slightly above this. The concentration of the introduced primary polyamine in the solvent is 2-20% by weight. The amount of phosgene added to the stream circulated by pumping is from 5 to 20 mol of phosgene per mol of amino groups in the polyamine solution added. As inert organic solvent, use is made of chlorobenzene or ortho-dichlorobenzene.

GB 1212249 describes a process for preparing isocyanates in which an excess of phosgene is reacted with a forward-directed, mixed film of the amine in an inert solvent in the first stage. A cylindrical tube is regarded as suitable for producing this film.

JP 57-048954 describes a process for preparing organic isocyanates in which the solution of a primary amine is introduced just upstream of the feed point of a static mixer which is located in a circulation reactor. A solution of phosgene in an organic isocyanate circulates in the circulation reactor.

Phosgenation in a loop reactor is also described in JP 60-10774 in which an isocyanate-containing reaction mixture is circulated by pumping. However, high yields are only achieved at amine concentrations of 5-10%.

The low temperatures in the first stage and the high temperatures in the second stage of loop reactor or mixing circuit processes are energetically disadvantageous. Since the reaction between an organic amine and phosgene is strongly exothermic, intensive cooling has to be employed in the first step in order to maintain the desired reaction temperature.

The second reaction, viz. the decomposition of the carbamoyl chloride to form the isocyanate, is significantly endothermic, so that the reaction mixture has to be heated again in the second stage.

Moreover, the significantly lower chemical yield compared to processes carried out in a single pass is particularly disadvantageous, since isocyanate already formed reacts with amine to form ureas in the mixing circuit due to backmixing. To suppress this secondary reaction, a low maximum steady-state isocyanate concentration is frequently permitted, but this in turn results in low space-time yields.

In the process described in EP 0716079 for the continuous preparation of organic isocyanates, the reaction mixture is circulated at 60-100° C. in a bubble column. The process described is carried out at slightly subatmospheric or slightly superatmospheric pressure, in general at 0.5-5 bar, preferably 1-3 bar.

EP 0570799 describes a process in which the reaction between amine and phosgene to form isocyanate is carried out in the gas phase. Gas-phase phosgenation is known for the preparation of aliphatic diisocyanates (EP 0289840,), aromatic diisocyanates (EP 0570799), cyclic diisocyanates (EP 1078918) and of triisocyanates (EP 0749958). EP 0749958, EP 0676392 and EP 0289840 describe processes for preparing aliphatic diisocyanates and triisocyanates by gas-phase phosgenation in which the reactants are mixed between nozzle and tube on entering the tube reactor described through nozzles or a combination of nozzles and an annular gap. A Reynolds number of RE>4700 in the tube is indicated as an essential criterion for mixing. A jet mixer is proposed in EP 0570799 for the preparation of aromatic diisocyanates by gas-phase phosgenation.

DE 1192641 describes a process for preparing isocyanates by reaction of primary aromatic or araliphatic amines with phosgene in the presence of solvents and subsequent heating of the reaction mixture, with the isocyanate which is to be prepared in the reaction being used as solvent.

DE 100 27 779 claims a process for preparing isocyanates by reacting amines with phosgene, in which the isocyanate is used as solvent and the reaction is carried out in a reaction column and the condensed phase at the bottom of the reaction column is recirculated in its entirety or in part to the enrichment section of the reaction column. The number of theoretical plates in the reaction column is 5-60. The temperature is from −20° C. to 300° C. and the absolute pressure is 0.2-60 bar.

U.S. Pat. No. 2,683,160 describes a process for preparing aromaticr isocyanates in which gaseous phosgene and a solution of an aromatic amine in a chlorinated aromatic hydrocarbon as solvent are introduced simultaneously into a solution of the desired isocyanate in the abovementioned solvent. The solution of the desired isocyanate in the solvent is maintained at the boiling point of the solvent, i.e. at 130° C.-300° C., with the solution boiling under reflux. The by-product hydrogen chloride and excess, unreacted phosgene are taken off continuously through the reflux condenser. The excess of phosgene is at least 50%, preferably from 80 to 100%, of the stoichiometric amount. The amine concentration in the solvent is from 5 to 30%, preferably from 8 to 12%. The reaction is carried out in a single apparatus which is stirred well and heated sufficiently.

DE 2252068 describes a process for preparing organic isocyanates from amine and phosgene, in which the amine which has been preheated to a temperature below its decomposition temperature at superatmospheric pressure is firstly reacted with preheated phosgene in the presence of an excess of an organic isocyanate as solvent at temperatures and pressures such that the reaction proceeds in a homogeneous, liquid phase and the organic carbamoyl chloride formed as intermediate is subsequently thermally dissociated at a lower pressure in a second stage. In a preferred embodiment, the first reaction stage is carried out adiabatically. The reaction components are fed in at temperatures in the range 120-180° C. The temperature of the reaction mixture at the outlet is maintained at 180-250° C. and the pressure is maintained at 100-300 atm. The residence time of the components in the first reaction zone should be 5-150 seconds. The second reaction stage is carried out isothermally. The feed temperature is 120-250° C. and the pressure is 3-30 atm. The residence time is 3-30 minutes. The isocyanate taken off from the second stage is cooled to 50-80° C. prior to recirculation.

U.S. Pat. No. 3,801,518 describes a process for preparing tolylene diisocyanate having an increased acidity of 0.03-0.3% by weight. This is achieved by phosgenation of toluenediamine and subsequent residence of the reaction product in a phosgene atmosphere at 100-200° C. for a period of at least 0.08 hour, preferably from 0.08 hour to 2 hours.

U.S. Pat. No. 3,912,600 describes the reduction in the acidity and the content of hydrolyzable chlorine in a polymethylene-polyphenylene polyisocyanate (PMDI) by treatment of this in an inert, organic solvent at a pressure of 20-60 psia and a temperature of 150-230° C., with removal of volatile compounds, known as low boilers.

GB 1196008 describes a continuous process for preparing aromatic monoisocyanates or diisocyanates by phosgenation of the corresponding amines in an organic solvent at 120-200° C. in two reaction vessels coupled to one another, with the excess of phosgene over the calculated stoichiometric amount being 5-20%.

It is an object of the present invention to develop a two-stage or multistage process which gives isocyanates in very high chemical yields and with high space-time yields at a low phosgene holdup.

It has surprisingly been found that, contrary to generally prevailing opinion, the second reaction, viz. the phosgenation of the amine hydrochloride, proceeds at a high reaction rate at high phosgene concentrations and elevated temperatures. High pressures are therefore advantageous for this reaction, since high pressures imply high phosgene concentrations in the liquid phase. Furthermore, elevated temperatures are advantageous for achieving high space-time yields. I. I. Konstantinov, A. I. Kormucheshkina, Zhurnal Prikladnoi Khimii, 49 (3), pp. 596-599, 1976) state that the phosgenation of the amine hydrochloride is very slow and is the rate-determining step of the overall reaction cycle to the isocyanate. Konstantinov et al. present kinetic measurements and quantify the reaction rates. According to them, the reaction rate for the phosgenation of the hydrochloride is considerably lower than that for the free amine. As described in GB 1212249, the formation of amine hydrochloride also leads to a loss of isocyanate yield due to urea formation. Since the solubility of amine hydrochlorides in the corresponding reaction mixtures and also in most commercially available solvents is very low, hydrochloride formation also drastically increases the problem of solids formation.

DE 3323882 describes a continuous process for the hot phosgenation of amine hydrochloride or mixtures thereof with carbamoyl chloride suspended in solvents by means of excess phosgene at from 80° C. to 200° C., preferably from 100° C. to 180° C. In this process, the solids are retained in the reactor by means of a suitable separation device and the isocyanate which is formed during the reaction and is present as a solution in the solvent is continuously taken off from the reactor. The solids are preferably separated off by means of a filter. Disadvantages of this process for phosgenation of hydrochlorides are the complicated solids handling, the risk of blockage of pipes and, in particular, of regulating valves and flowmeters and also the long residence time which requires large apparatuses and results in a high phosgene holdup and also the severe reaction conditions and the relatively low yields.

DE 2404773 describes a process for preparing monoisocyanates, diisocyanates and/or polyisocyanates from organic primary amines and phosgene, in which the primary amines are mixed with at least 3 mol of phosgene per amino group in the absence of a solvent and the reaction mixture is simultaneously broken up to a mean particle size of 1-100 μm and the resulting suspension of carbamoyl chloride and amine hydrochloride in phosgene is converted into the corresponding isocyanates at from 100 to 180° C., preferably from 120 to 160° C., and pressures of from 14 to 55 bar, preferably from 21 to 41 bar. The process is a two-stage process in which the starting materials primary amine and phosgene are mixed in the first step at from −30° C. to 60° C., preferably 0-50° C., at atmospheric pressure or preferably superatmospheric pressure, in particular at from 14 to 55 bar, and at the same time the particles are comminuted to a mean particle size of from 1 to 100 μm, preferably from 1 to 50 μm. The amine is added as a liquid, melt or possibly as a powder to the phosgene. Various mixing and comminution devices are described. The second stage comprises the reaction of amine hydrochloride with phosgene to form carbamoyl chloride and its decomposition into isocyanate and hydrogen chloride in a pressure vessel at 100-180° C., preferably from 120 to 160° C., and pressures of 14-55 bar, preferably from 21 to 41 bar. This process is technically very complicated and not economical.

DE-A 156844 likewise describes a phosgenation of an amine hydrochloride suspension which is carried out at elevated temperature in a multistage cascade of stirred vessels. A particular disadvantage of a cascade of stirred vessels is the high phosgene holdup.

It has now surprisingly been found that the phosgenation of the amine hydrochloride is a fast reaction at high phosgene concentrations and elevated temperatures.

Furthermore, it has surprsingly been found that amine hydrochloride and carbamoyl chloride formed in situ display a high level of supersaturation in the reaction mixture when a static mixer, preferably a nozzle, is used as reactor for the first stage. Even when amine hydrochloride and/or carbamoyl chloride precipitate, the process claimed has considerable advantages since a very narrow amine hydrochloride particle size distribution having a very small mean particle diameter, usually in the nanometer to micron range, can be produced when using a static mixer, preferably a nozzle, as reactor for the first stage as a result of the introduction of high mixing energies. However, it is more advantageous to achieve high conversions or if possible complete conversion in the phosgenation of amine hydrochloride before solid amine hydrochloride or carbamoyl chloride precipitates in relatively large amounts, since solids handling is complicated from a process engineering point of view and can lead to caked material and blockages and, secondly, the phosgenation of large and agglomerated amine hydrochloride particles as described in the literature is very slow.

The present invention accordingly provides a process for preparing polyisocyanates by reacting organic amines with phosgene, wherein the reaction is carried out in at least three stages, with the first stage being carried out in a mixing apparatus, the second stage in at least one residence apparatus and the third stage in at least one separation apparatus and the pressure in each successive stage being lower than that in the previous stage.

The first stage of the process of the present invention comprises essentially the reaction of the amine to carbamoyl chloride and amine hydrochloride, the second stage comprises essentially the reaction of the amine hydrochloride formed in the first stage to give carbamoyl chloride and the third stage comprises essentially the dissociation of the carbamoyl chloride into isocyanate and hydrogen chloride.

In the process of the present invention, the reaction between organic amine and phosgene is carried out in three or more stages in an inert solvent, preferably toluene or chlorobenzene, dichlorobenzene or mixtures thereof, using an excess of phosgene, with the pressure being reduced from stage to stage. The first phosgenation stage comprises a static mixer, preferably a nozzle. The pressure upstream of the nozzle is preferably from 3 to 70 bar, in particular from 15 to 45 bar. The pressure difference over the nozzle is at least 0.5 bar. The temperature in the first stage is preferably from 80 to 190° C., in particular from 90 to 150° C. The second stage comprises one or more residence apparatuses, preferably one residence apparatus, which is operated at a pressure of from 2.5 to 35 bar, preferably from 15 to 35 bar. Downstream of the nozzle, the reaction mixture is depressurized by means of a regulating valve or some other device suitable for this purpose to the pressure of the residence apparatus of the second stage. However, the natural pressure drop of the nozzle can also be used for the pressure reduction.

The reactor of the first stage can also be integrated into the reactor of the second stage. In particular, a mixing nozzle can dip into the gas phase or preferably into the liquid phase of the second reactor, i.e. can be located entirely or partly therein. It is also possible for the output from the nozzle to be conveyed by means of a pipe, an immersed tube or a plug-in tube into the gas phase or preferably into the liquid phase of the reactor of the second stage.

The temperature in the second stage is from 80 to 190° C., preferably from 90 to 150° C. Possible types of reactor for the second stage are tube reactors, stirred vessels, unstirred residence apparatuses, phase separation apparatuses and other apparatuses. The reactor can also be provided with a pumped circuit which may in turn have a heat exchanger for setting the reaction temperature. In the case of a stirred vessel, an unstirred residence apparatus or possibly also in the case of a phase separation apparatus, the liquid phase is preferably depressurized under level control and the gas phase is depressurized under pressure control into the reactor of the third stage. However, the gas phase, which comprises mainly phosgene, hydrogen chloride and possibly solvent, can also be passed directly to the work-up, e.g. fractionation into phosgene, hydrogen chloride and solvent or into mixtures thereof. The residence reactor of the second stage can, depending on the desired residence time and capacity of the plant, have relatively large dimensions and volumes, which can be regarded as disadvantageous from the point of view of cost or safety, e.g. phosgene holdup at high pressure. In this case, the reactor of the second stage can be realised as two or more similar or different reactors and types of reactor, which can be connected in parallel or, if appropriate to influence the residence time spectrum, also in series.

The reactor of the third stage of the process of the present invention is operated at a pressure of from 2 to 20 bar, preferably from 3.5 to 16 bar. Downstream of the residence reactor of the second stage, the reaction mixture is depressurized to the pressure of the third reactor by means of a regulating valve or some other device suitable for this purpose. A natural pressure drop may also be able to be utilized.

In any case, the pressure in the following stage is, as described above, selected so that it is lower than in the previous stage.

The temperature in the third stage is from 80 to 190° C. The reactor used for the third stage is a column, in particular a reaction column as is described, for example, in WO 99/54289. The temperature at the bottom is from 80 to 190° C. and the temperature at the top is from 50 to 120° C. The column used as reactor of the third stage can also be utilized for removing the excess phosgene from the reaction mixture. The reactor of the third stage can, like the reactor of the second stage, be disadvantageously large. In this case, the reactor of the third stage can also be realised as two or more similar or different columns connected in series. The output from the bottom of the reaction column is worked up by customary methods to remove any phosgene still present and to separate off the solvent. In the case of the preparation of TDI, the crude TDI is subsequently subjected to removal of high boilers and purification by distillation. Phosgene, hydrogen chloride and possibly solvent can be separated off in a known manner from the vapor leaving the reaction column and, if appropriate, the residence reactor of the second stage and can, if appropriate, be recirculated.

As solvents, preference is given to using chlorinated aromatic hydrocarbons such as dichlorobenzene, chlorobenzene, trichlorobenzene or mixtures thereof, aromatic or aliphatic hydrocarbons such as toluene, xylene, benzene, pentane, hexane, heptane, octane, cyclohexane, biphenyl, ketones such as 2-butanone, methyl isobutyl ketone, esters such as diethyl isophthalate, ethyl acetate, butyl acetate, nitriles such as acetonitrile and also sulfolane.

The particular advantage of the process of the present invention is that, in contrast to the processes customary in the prior art, the two reaction steps 1) phosgenation of the amine hydrochloride to form carbamoyl chloride and 2) decomposition of the carbamoyl chloride into isocyanate and hydrogen chloride are carried out partly or entirely in separate stages or reactors and very high chemical yields, very high space-time yields and at the same time a very low phosgene holdup can be achieved as a result of the independent setting of the optimum pressure and optimum temperature for the respective reaction and the selection of the most favorable reactor design in each case. The synthesis can be carried out adiabatically or isothermally. The differing apparatus design optimally takes account of the conditions of the two reactions. While the phosgenation of the amine hydrochloride requires high pressures, low pressures are advantageous for the decomposition of the carbamoyl chloride. Furthermore, the residence times selected for the reactor for the phosgenation of the amine hydrochloride can be shorter than those for the decomposition of the carbamoyl chloride, which considerably reduces the overall phosgene holdup. Furthermore, removal, in particular by stripping, of the gaseous hydrogen chloride formed is advantageous for the decomposition of the carbamoyl chloride because the carbamoyl chloride/isocyanate equilibrium is in this way advantageously shifted to the side of the desired isocyanate. This can be taken into account by the choice of a (reaction) column as optimum reactor design. The excess phosgene can also be removed at the same time. This is not absolutely necessary in this stage, and can also be carried out in a further stage. In contrast, the removal of hydrogen chloride in the residence reactor of the second stage would be very disadvantageous, since the phosgene necessary for the phosgenation of the amine hydrochloride would in such a case also be removed together with the hydrogen chloride. Vaporizing phosgene also leads to cooling of the reaction mixture, which could lead to massive precipitation of solid carbamoyl chloride and amine hydrochloride.

The rapid reaction between amine and phosgene to form carbamoyl chloride and hydrogen chloride and also amine hydrochloride requires high pressures in both the first and second stages to achieve high phosgene concentrations in the liquid phase and thus high excesses of phosgene if good chemical yields are to be obtained as a result of low by-product formation. In addition, good mixing is necessary, i.e. a static mixer, preferably a nozzle should be used as apparatus. High admission pressures upstream of the nozzle allow high pressure drops over the nozzle and thus the introduction of high mixing energies.

Dissolved amine hydrochloride and very small amine hydrochloride particles surprisingly react very quickly with phosgene in the residence reactor of the second stage and therefore do not require a long residence time. High phosgene concentrations are advantageous here. Relatively high pressures do not have an adverse effect on the phosgenation of the amine hydrochloride, so that high phosgene concentrations in the liquid phase can advantageously be set by means of relatively high pressures. Suitable apparatuses are, in particular, tube reactors, stirred vessels, unstirred residence apparatuses, phase separation apparatuses or other residence apparatuses. Furthermore, heatable embodiments of these apparatuses are advantageous in order to compensate, if appropriate, temperature drops caused by the endothermic decomposition of the carbamoyl chloride. The reaction of the third stage, viz. the dissociation of the carbamoyl chloride into isocyanate and hydrogen chloride, is a pressure-dependent equilibrium reaction. It is advantageously shifted to the side of the desired isocyanate by low pressures. Since this reaction does not require any phosgene, the low phosgene concentrations in the liquid phase characteristic of low pressures do not interfere and in fact lead to a low phosgene holdup in the reactor of the third stage, which is advantageous from a safety point of view. In this way, the overall phosgene holdup in the process, and possibly also in the individual apparatuses, can be significantly reduced compared to a cascade of stirred vessels or a reaction tower. High pressures are, in contrast, very unfavorable for the dissociation of carbamoyl chloride and require long residence times, high temperatures and energy consumptions, since at high pressures the equilibrium lies far on the side of the carbamoyl chloride. Long residence times in turn result in a high phosgene holdup. A (reaction) column as described, for example, in WO 99/54289 (DE 19817691) is particularly useful as apparatus for the third stage. In addition the stripping effect shifts the carbamoyl chloride/isocyanate equilibrium advantageously to the side of the desired isocyanate.

The phosgenation of the amine hydrochloride does not have to be completed in the second stage, and it is likewise possible for the decomposition of the carbamoyl chloride to start in the second stage. However, preference is given to a design of the reactor of the second stage in terms of residence time and other process engineering parameters which is such that the phosgenation of the amine hydrochloride is virtually complete and the decomposition of the carbamoyl chloride has not yet progressed to any large extent.

If the phosgenation of the amine hydrochloride and the decomposition of the carbamoyl chloride are, as described in the prior art, carried out in one stage or in one reactor, the high pressure required for the phosgenation of the amine hydrochloride results in a low conversion of the carbamoyl chloride into the isocyanate and thus long residence times. A high phosgene concentration and long residence times (large reaction volumes) in turn result in a very high phosgene holdup. This is present at high pressures and temperatures which are of concern from a safety point of view. Physical separation of the two reactions, viz. the phosgenation of the amine hydrochloride in the second phosgenation stage at a high pressure and the decomposition of the carbamoyl chloride in the third phosgenation stage at a low pressure, enables high chemical yields, high space-time yields and especially a low phosgene holdup in the overall process and possibly also in the individual apparatuses to be achieved.

Physical separation of the first and second stages is not absolutely necessary, since a high pressure increases the phosgene concentration in the liquid phase, which favors both the first reaction between amine and phosgene and the second reaction between amine hydrochloride and phosgene.

Furthermore, the process can be carried out at elevated temperature and if desired also isothermally in all stages. This results, in particular, in high space-time yields and thus low phosgene holdups and smaller apparatuses together with simultaneously higher chemical yields, especially compared to the classical cold/hot phosgenation. In addition, avoiding cooling of the reaction mixture in the first stage and subsequent reheating in the second stage and the following stages saves a considerable quantity of energy. Avoiding the precipitation of amine hydrochloride as solid enables long residence times, which can sometimes be realised only by means of a circulation mode of operation (loop reactors), to be avoided. Although the circulation mode of operation likewise involves a lower phosgene holdup than, for example, a cascade of stirred vessels, it suffers from increased formation of by-products, in particular ureas. To avoid urea formation, the amine or isocyanate concentration has to be kept low, which leads to very low space-time yields.

The temperatures and pressures employed are to some extent dependent on the amine used. Likewise, the phosgene excesses and residence times to be employed in the individual apparatuses are dependent on the amine used. In the case of diphenylmethane diisocyanates (MDI) and/or polyphenylene-polymethylene polyisocyanates (PMDI) or mixtures of these two, the excess of phosgene should be at least 100% of the stoichiometric amount, while in the case of tolylene diisocyanate (TDI), it should at least 300% of the stoichiometric amount and in the case of hexamethylene diisocyanate (HDI) and isophorone diisocyanate (IPDI) it should likewise be at least 300% of the stoichiometric amount. The residence time in the first stage (static mixer) is naturally very short and is defined by the apparatus design. The mean residence time in the residence apparatus of the second stage can be from one second to 30 minutes. Preference is given to mean residence times of from 30 seconds to 10 minutes, particularly preferably from 2 to 7 minutes. The mean residence time in the apparatus of the third stage (reaction column) is dependent on the number of theoretical plates, the height of the weir, the volume of liquid phase, the throughput through the column and other process engineering parameters. It is preferably not more than 1 hour.

The amine concentration in the inert solvent is likewise dependent on the amine used and on the solvent. In the case of diphenylmethanediamine (MDA) and/or polyphenylene-polymethylenepolyamines (PMDA) or mixtures of these two, it can be 5-50% by weight, preferably 25-40% by weight; in the case of toluenediamine (TDA) it can be 5-50% by weight, preferably 15-30% by weight; in the case of hexamethylenediamine (HDA) it can be 5-50% by weight, preferably 15-30% by weight; and in the case of isophoronediamine (IPDA) it can likewise be 5-50% by weight, preferably 15-30% by weight. The phosgene concentration in the inert solvent can be 0-70% by weight, preferably 10-50% by weight. Preference is given to using the same solvent as for the amine. It is also possible to omit a solvent entirely.

The invention is illustrated by the following examples.

EXAMPLES

1a) Tube Reactor as Residence Apparatus (I)

A solution of 0.73 kg/h of toluenediamine (TDA) in 3.3 kg/h of chlorobenzene was reacted at 110° C. with 6.2 kg/h of phosgene in a mixing nozzle. The pressure drop over the nozzle was 6 bar. The reaction mixture was depressurized directly into a tube reactor heated by means of a double wall as residence apparatus having a residence time of 2 minutes at 110° C. and a pressure of 15 bar abs. The output from the tube reactor was depressurized via a regulating valve into a bubble cap tray column (reaction column). The temperature at the bottom of the reaction column was 150° C. and the pressure at the top was 3.5 bar abs. At the top of the column, a mixture (5.8 kg/h) of phosgene (4.8 kg/h, 82% by weight), hydrogen chloride (0.85 kg/h, 15% by weight) and chlorobenzene (0.19 kg/h, 3% by weight) and small amounts of various low boilers ($CCl_4$, $CHCl_3$, $N_2$, CO, $CO_2$) was taken off, partially condensed and passed to hydrogen chloride/phosgene separation by a known method. Part of the condensate was returned to the column as runback. The temperature at the top was 71° C. At the bottom of the column, a mixture (4.4 kg/h) of tolylene diisocyanate (1.0 kg/h, 23% by weight), chlorobenzene (3.1 kg/h, 70% by weight), phosgene (0.27 kg/h, 6% by weight), hydrogen chloride (0.02 kg/h, 0.5% by weight) and small amounts of high boilers (0.04 kg/h, 1% by weight) was taken off. A shell-and-tube apparatus having 13 tubes was used as bottom circulation vaporizer.

1b) Tube Reactor as Residence Apparatus (II)

A solution of 0.73 kg/h of toluenediamine (TDA) in 3.2 kg/h of chlorobenzene was reacted with 6.2 kg/h of phosgene in a mixing nozzle. The pressure drop over the nozzle was 8 bar. The reaction mixture was depressurized directly into a tube reactor as residence apparatus having a residence time of 10 seconds at 120° C. and a pressure of about 15 bar abs. The output from the tube reactor flowed directly into a bubble cap tray column. The temperature at the bottom of the reaction column was 150° C. and the pressure at the top was 15 bar abs. At the top of the column, a mixture (3.0 kg/h) of phosgene (2.1 kg/h, 71% by weight) and hydrogen chloride (0.85 kg/h, 29% by weight) and small amounts of chlorobenzene and various low boilers ($CCl_4$, $CHCl_3$, $N_2$, CO, $CO_2$) was taken off, partially condensed and passed to hydrogen chloride/phosgene separation by a known method. Part of the condensate was returned to the column as runback. At the bottom of the column, a mixture (kg/h) of tolylene diisocyanate (1.0 kg/h, 14% by weight), chlorobenzene (3.2 kg/h, 45% by weight), phosgene (2.9 kg/h, 41% by weight) and small amounts of high boilers (0.05 kg/h, 1% by weight) was taken off. A shell-and-tube apparatus having 13 tubes was used as bottom circulation vaporizer.

2) Stirred Vessel as Residence Apparatus

A solution of 0.73 kg/h of toluenediamine (TDA) in 3.3 kg/h of chlorobenzene was reacted at 140° C. with 6.2 kg/h of phosgene in a mixing nozzle. The pressure drop over the nozzle was 4 bar. The nozzle was integrated into a tube reactor as residence reactor into which the reaction mixture was depressurized. The residence reactor was a stirred vessel which was brought to a temperature of 140° C. via the double wall. The stirrer speed was 1000 revolutions per minute. As an alternative, the nozzle was placed outside the residence reactor and the output from the nozzle was fed directly into the liquid phase via a plug-in tube. Depressurization into the gas phase led to somewhat lower yields of tolylene diisocyanate (TDI). The liquid phase is discharged under level control and the gas phase is discharged under pressure control from the residence reactor into a bubble cap tray column (reaction column). The stirred vessel was operated in the pressure range from 2.5 to 35 bar abs. The mean residence time of the liquid phase (regulated via the level) was up to 30 minutes. The stirred vessel was also operated with an external loop provided with a heat exchanger (pumped circuit with gear pump). The temperature at the bottom of the reaction column is 110° C. and the pressure at the top is 3.5 bar abs. At the top of the column, a mixture (5.0 kg/h) of phosgene (4.0 kg/h, 20% by weight), hydrogen chloride (0.85 kg/h, 17% by weight) and chlorobenzene (0.16 kg/h, 3% by weight) and small amounts of various low boilers ($CCl_4$, $CHCl_3$, $N_2$, CO, $CO_2$) is taken off, partially condensed and passed to hydrogen chloride/phosgene separation by a known method. Part of the condensate was returned to the column as runback. The temperature at the top was 70° C. At the bottom of the column, a mixture (5.2 kg/h) of tolylene diisocyanate (1.0 kg/h, 19% by weight), chlorobenzene (3.1 kg/h, 59% by weight), phosgene (1.15 kg/h, 22% by weight), hydrogen chloride (0.02 kg/h, 0.3% by weight) and small amounts of high boilers (0.02 kg/h, 0.4% by weight) was taken off. A shell-and-tube apparatus having 13 tubes was used as bottom circulation vaporizer.

3) Phase Separation Apparatus

A solution of 0.74 kg/h of diaminodiphenylmethane (MDA) in 1.6 kg/h of chlorobenzene was reacted with a solution of 1.9 kg/h of phosgene in 2.1 kg/h of chlorobenzene in a mixing nozzle. The pressure drop over the nozzle was 5 bar. The nozzle was depressurized via a plug-in tube into the liquid phase of a phase separator. The pressure downstream of the nozzle was 12 bar and the temperature was 115° C. The liquid phase and the gas phase were conveyed separately into a bubble cap tray column (reaction column). The mean residence time of the liquid phase was about 3 minutes. The temperature at the bottom of the reaction column was 115° C. and the pressure at the top was 5 bar abs. At the top of the column, a mixture (1.5 kg/h) of phosgene (0.73 kg/h, 50% by weight), hydrogen chloride (0.50 kg/h, 33% by weight) and chlorobenzene (0.24 kg/h, 16% by weight) and small amounts of various low boilers ($CCl_4$, $CHCl_3$, $N_2$, CO, $CO_2$) was taken off, partially condensed and passed to hydrogen chloride/phosgene separation by a known method. Part of the condensate was returned to the column as runback. The temperature at the top was 110° C. At the bottom of the column, a mixture (4.9 kg/h) of methylenedi(phenyl isocyanate) (MDI, 0.93 kg/h, 19% by weight), chlorobenzene (3.5 kg/h, 71% by weight), phosgene (0.43 kg/h, 9% by weight) and hydrogen chloride (0.05 kg/h, 1.0% by weight) was taken off. A shell-and-tube apparatus having 13 tubes was used as bottom circulation vaporizer.

We claim:

1. A process for preparing at least one polyisocyanate comprising reacting organic amines with phosgene in an inert solvent, wherein the reaction is carried out in at least three stages, with the first stage being carried out in a mixing apparatus, the second stage in at least one residence apparatus and the third stage in at least one reaction column and a pressure in each successive stage being lower than that in the previous stage wherein in said third stage, a carbamoyl chloride is dissociated into isocyanate and hydrogen chloride, and wherein the pressure is reduced from the pressure of the mixing apparatus of the first stage to the pressure of the residence apparatus of the second stage by a first regulating device, and wherein the pressure is reduced from the pressure of the at least one residence apparatus of the second stage to the pressure of the at least one reaction column by a second regulating device.

2. The process of claim 1, wherein the at least one polyisocyanate is diphenylmethane diisocyanate (MDI), polyphenylene-polymethylene polyisocyanate (PMDI), tolylene diisocyanate (TDI), hexamethylene diisocyanate (HDI), isophorone diisocyanate (IPDI), or a mixture of diphenylmethane diisocyanate (MDI) and polyphenylene-polymethylene polyisocyanate (PMDI).

3. The process of claim 1, wherein a nozzle is used as the mixing apparatus for the first stage.

4. The process of claim 1, wherein a tube reactor, a stirred vessel, an unstirred residence apparatus or a phase separation apparatus for gas and liquid phases is used as the at least one residence apparatus for the second stage.

5. The process of claim 1, wherein the residence time in the residence apparatus of the second stage is from 1 second to 30 minutes.

6. The process of claim 1, wherein the at least one residence apparatus of the second stage comprises at least two reactors of the same or different types which are connected in parallel, in series, or in a combination thereof.

7. The process of claim 1, wherein the phosgene is separated off in the at least one reaction column of the third stage.

8. The process of claim 1, wherein the mixing apparatus of the first stage is integrated into the at least one residence apparatus of the second stage.

9. The process of claim 1, wherein the pressure upstream of the mixing apparatus is 3-70 bar.

10. The process of claim 1, wherein the temperature in the first, second and third stages is in each case 80-190° C.

11. The process of claim 1, wherein an aromatic hydrocarbon, a chlorinated aromatic hydrocarbon, or a mixture thereof is used as the inert solvent.

12. The process of claim 1, wherein the residence time in the at least one residence apparatus of the second stage is from 30 seconds to 10 minutes.

13. The process of claim 1, wherein the residence time in the at least one residence apparatus of the second stage is from 2 to 7 minutes.

14. The process of claim 1, wherein the first regulating device is a regulating valve.

15. The process of claim 1, wherein the second regulating device is a regulating valve.

16. The process of claim 1, wherein the pressure upstream of the mixing apparatus is 15-45 bar.

17. The process of claim 1, wherein the pressure in the reactor of the second stage is 2.5-35 bar.

18. The process of claim 1, wherein the temperature in the first, second and third stages is in each case 90-150° C.

* * * * *